United States Patent [19]
Lewis et al.

[11] Patent Number: 5,441,707
[45] Date of Patent: Aug. 15, 1995

[54] STERILIZATION CONTAINER

[75] Inventors: Paul P. Lewis, Warsaw; Daniel Owens; Daniel L. Sands, both of Silver Lake, all of Ind.

[73] Assignee: Paragon Group of Plastics Companies, Inc., Warsaw, Ind.

[21] Appl. No.: 317,236

[22] Filed: Oct. 3, 1994

[51] Int. Cl.⁶ .............................................. A61L 2/00
[52] U.S. Cl. ................... 422/300; 422/292; 206/514; 206/438; 206/439; 220/23.86
[58] Field of Search .................. 422/292, 297, 300; 206/372, 373, 438, 439, 505, 506, 507, 514, 558; 220/23.86, 408, 410; 62/457.7

[56] References Cited

U.S. PATENT DOCUMENTS

| | | | |
|---|---|---|---|
| 3,241,706 | 3/1966 | Monaco et al. | 206/558 |
| 3,270,913 | 9/1966 | Bridenstine et al. | 206/507 |
| 3,493,722 | 2/1970 | Popeil | 422/300 |
| 3,791,547 | 2/1974 | Branscum | 220/410 |
| 4,106,623 | 8/1978 | Carroll et al. | 206/507 |
| 4,515,421 | 5/1985 | Steffes | 62/457.7 |
| 5,098,676 | 3/1992 | Brooks, Jr. | 422/292 |
| 5,344,022 | 9/1994 | Stahl | 206/507 |

*Primary Examiner*—Robert J. Warden
*Assistant Examiner*—Theresa T. Snider
*Attorney, Agent, or Firm*—Baker & Daniels

[57] ABSTRACT

A sterilization container for sterilizing and storing medical instruments includes a base tray and one or more insert trays removably mounted in a cavity defined by the side and bottom walls of the base tray. Insert trays are supported on ribs projecting transversely into the base tray cavity which cooperates with the side walls of the base tray to define a groove which receives a circumferential wall defined on a turned over portion of an insert tray, thereby inhibiting the latter from migrating to the bottom of the base tray. The ribs have lateral side surface to engage the circumferentially extending wall of the insert trays to restrict lateral movement of the insert trays relative to the base tray to that distance which brings the circumferentially extending walls of the base tray into engagement with the lateral surface of one of the ribs.

13 Claims, 3 Drawing Sheets

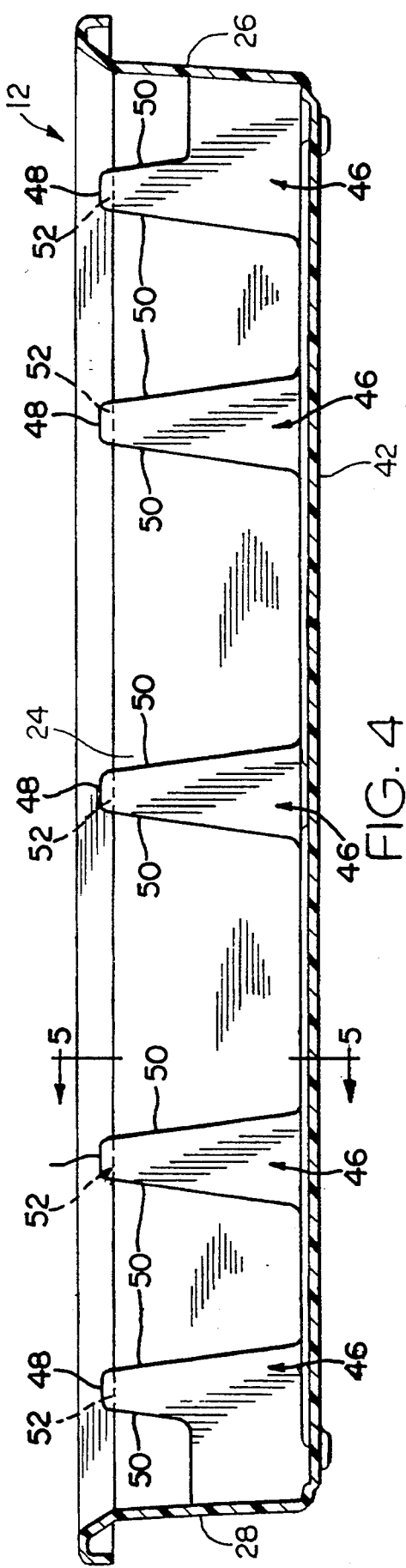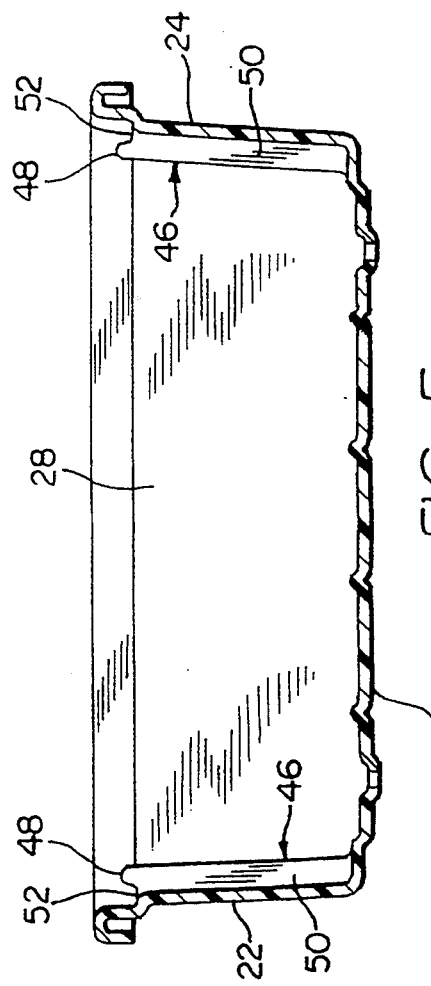

STERILIZATION CONTAINER

BACKGROUND OF THE INVENTION

This invention relates to a container for sterilizing medical instruments.

Sterilization containers are used for sterilizing, storing, and transporting medical instruments. Sterilization containers generally are elongated containers having bottom and side walls providing an open cavity which is closed by a removable lid during sterilization. Prior art sterilization container is disclosed in U.S. Pat. No. 5,098,676 (Brooks). The sterilization tray disclosed in Brooks provides a single layer, relatively shallow container which stores medical instruments on a single level. It is, however, desirable to package different types of medical instruments in different containers. To facilitate handling, it is desirable that customized assortments of medical instruments be made available, which are prepackaged and then assembled in a modular arrangement for use. Accordingly, it is desirable to provide the greatest possible flexibility in providing instrument containment so that the necessary instruments may be combined in separate trays and transported as a unit for use.

SUMMARY OF THE INVENTION

Accordingly, the present invention provides a "modular" sterilization container, in which a relatively large base tray is provided which has bottom and side walls defining an instrument receiving cavity. Insert trays of varying sizes are provided which fit within the larger base tray. One pair of the side walls of the base tray is provided with transversely projecting ribs which support the insert trays to prevent them from migrating to the bottom of the base tray. The ribs are also provided with lateral surfaces which engage a corresponding surface on the insert tray to prevent the insert trays from moving laterally within the base tray in excess of a predetermined distance. The insert trays are not as deep as the base tray, so that instruments may be stored in the base tray underneath one or more of the insert trays. Each of the base trays, insert trays, and removable lid are provided with openings to permit sterilization gases to reach the instruments. Each of the base and insert trays may be provided with supporting mats of the type disclosed in U.S. patent application 128,806, filed Sep. 29, 1993, and owned by the assignee of the present invention. Accordingly, the present invention provides the advantage of permitting medical instruments to be stored, sterilized and transported in any desired combination of separate trays, including a base tray and one or more insert trays that are supported within the base tray. Another advantage of the present invention is that ribs are provided on one pair of side walls of the base tray to engage the insert trays to prevent the latter from migrating to the bottom of the base tray and also to restrain movement of the insert trays laterally within the base tray.

BRIEF DESCRIPTION OF THE DRAWINGS

These and other advantages of the invention become apparent from the following descriptions, with reference to the accompanying drawings, in which:

FIG. 4 is a cross sectional view taken substantially along line 4—4 of FIG. 1; and FIG. 5 is a transverse cross sectional view taken substantially along lines 5—5 of FIG. 4.

DETAILED DESCRIPTION OF THE PREFERRED EMBODIMENT

Figure 1:
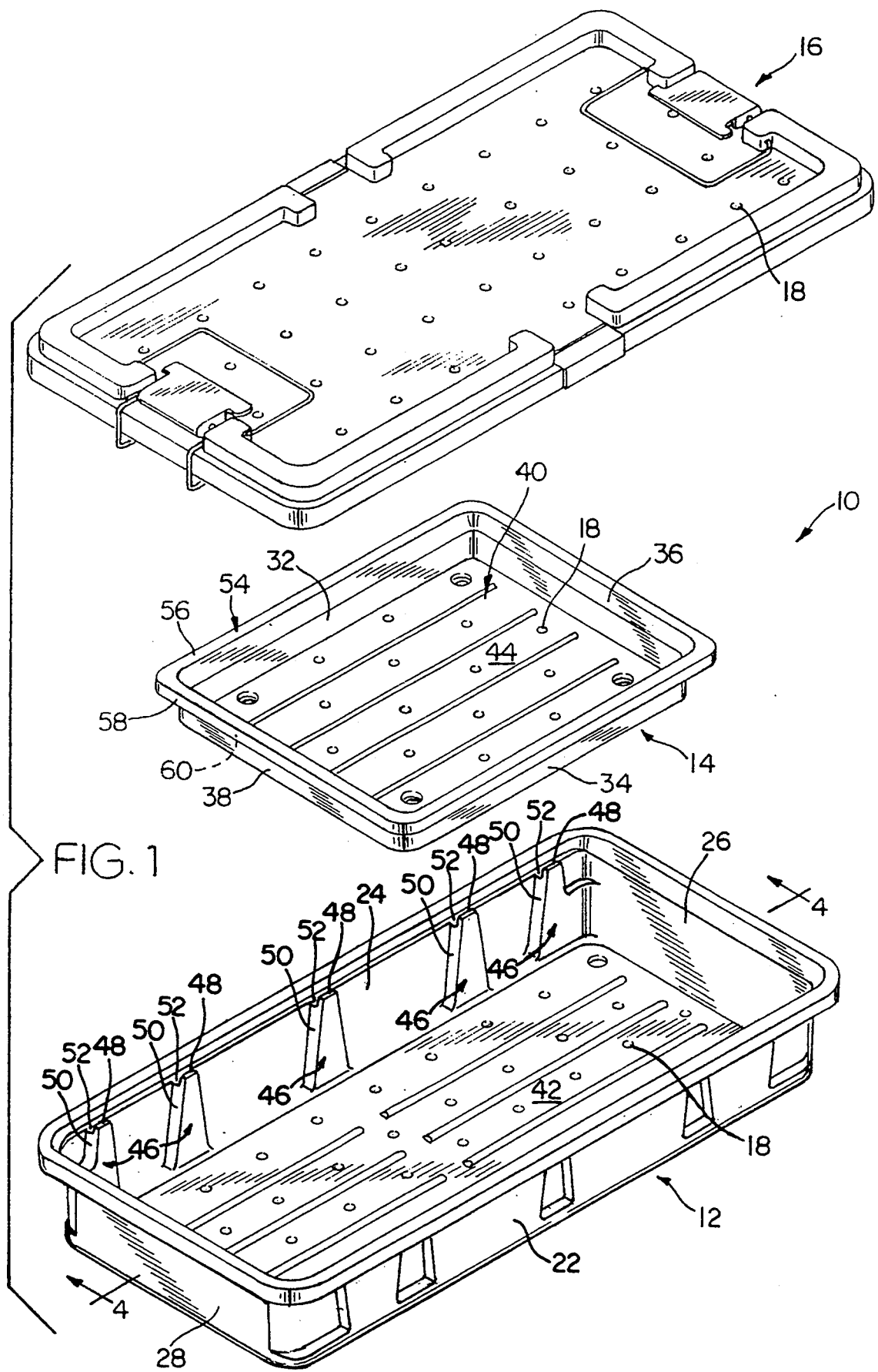
FIG. 1 is a exploded perspective view of sterilization container comprising a base tray, an insert tray, and a lid made pursuant to the teachings of the present invention.
Figure 2:
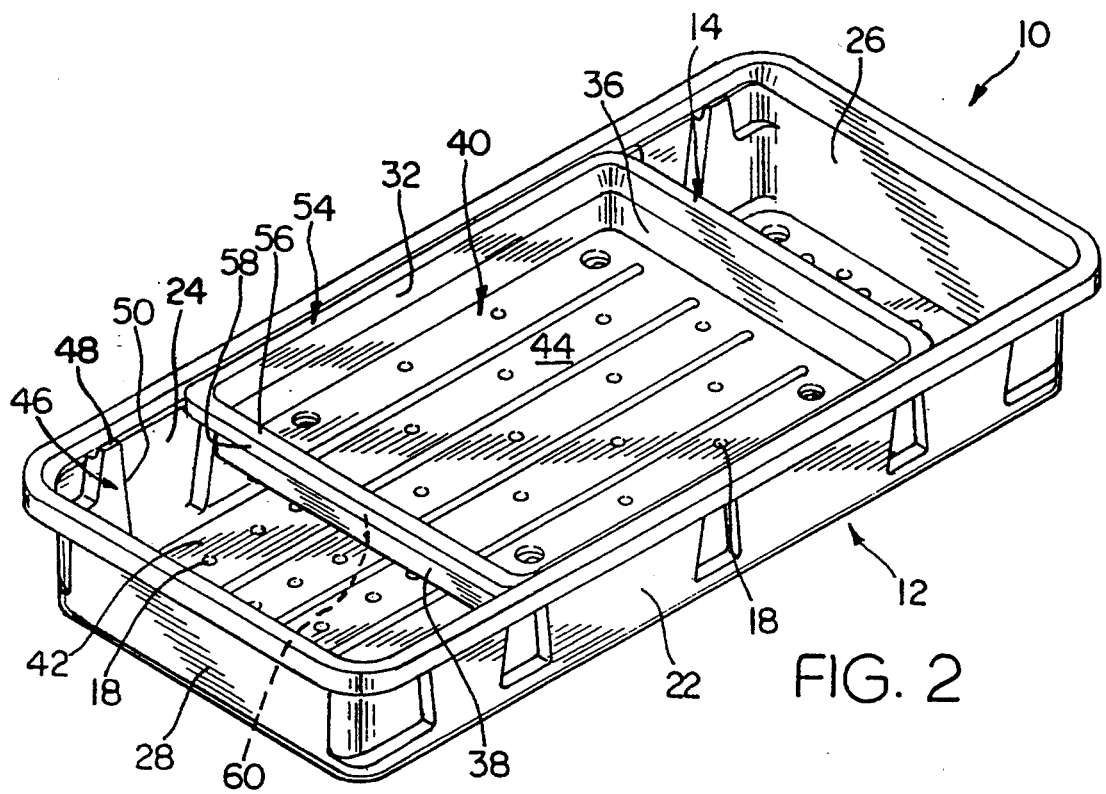
FIG. 2 is a perspective view of a sterilization container according to the present invention comprising a base tray and an insert tray disposed within the cavity defined by the base tray.
Figure 3:
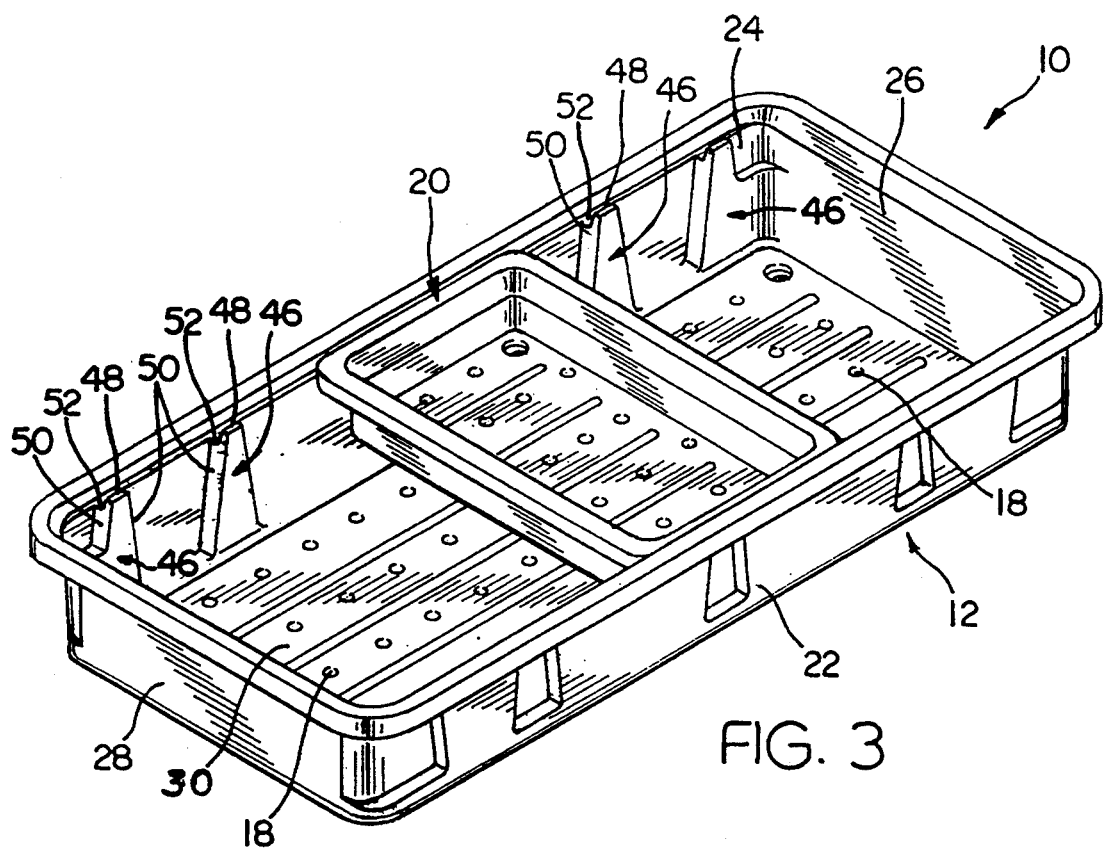
FIG. 3 is a view similar to FIG. 2 but illustrating a base tray of the same size as FIG. 2 with an insert tray of a size smaller than the insert tray illustrated in FIG. 2.

Referring now to the drawings, the sterilization container generally indicated by the numeral 10 includes a base tray 12, an insert tray 14 and a lid 16. Each of the base tray 12, insert tray 14 and lid 16 are provided with openings 18 which permit circulation of sterilization gases around the instruments (not shown). As can be seen in FIG. 3, insert tray 14 may be replaced by a smaller insert tray 20. Two or more of the smaller trays 20 may be used in a single base tray 12, and the location of a larger insert tray, such as the insert tray 14, may be varied from the intermediate position illustrated in FIG. 2 to positions to the left and right of the intermediate position illustrated. The base tray 12 includes a first pair of cooperating side walls 22, 24 which cooperate with a second pair of cooperating side walls 26, 28 and a bottom 42 to define a cavity 30. The insert trays 14, 20 are received within the cavity 30, and each consists of side walls 32, 34 and 36, 38 which cooperate with a bottom 44 to define a cavity 40. However, since the side walls 32, 34, 36, 38 are shorter than the side walls 22, 24, and 26, 28 of the base tray 12, the cavity 40 is less deep than is the cavity 30 of the base tray 12. Accordingly, instruments may be stored on the bottom 42 of the base tray 12 underneath the bottom 44 of the insert tray 40.

The sides 22, 24 of the base tray 12 are provided with longitudinally spaced, transversely projecting ribs 46 which project into the cavity 30. Each of the ribs 46 include an upwardly protruding peak 48 and inclined lateral surfaces 50. The protruding peaks 48 project above the lateral inclined surfaces 50, but terminate below the upper edge of the corresponding walls 22, 24. The projecting peaks 48 cooperate with the corresponding wall 22, 24 to define a gap 52 therebetween. Of course, the number and spacing of the ribs 46 may be varied as necessary to support insert trays of varying sizes.

The side walls 32, 34, 36, and 38 of the insert trays 14 and 20 include a turned over portion generally indicated by the numeral 54 at the upper edge of the walls. The turned over portion includes outwardly extending portions 56 which terminate in a downwardly projecting, circumferentially extending wall 58 that extends around all of the side walls 32-38. The circumferentially extending wall 58 and outwardly extending portion 56 cooperate with the side walls 32-38 to define a circumferentially extending groove 60 therebetween.

As can be seen from the drawings, the distance between the portion of the circumferentially extending wall 58 on side wall 32 and the portion of circumferentially extending wall 58 carried on side wall 34 is such that a circumferentially extending wall 58 on both of the side walls 32 and 34 is received in the corresponding gaps 52 between the ribs 46 and their corresponding side walls 22 and 24 of the base tray 12. Accordingly, the projecting peaks 48 on the ribs 46 extend into the groove 60, thereby providing positive support for the insert tray that prohibits the tray from migrating into the bottom of the base tray. Furthermore, as can best be seen in FIGS. 2 and 3, the lateral surfaces 50 of ribs 46 engage the circumferentially extending wall 58 of the side walls 36 and 38 to restrict lateral movement of the insert trays within the cavity 30 to a distance that permits the circumferentially extending wall 58 to engage the lateral surface 50 of one of the ribs 46. As illustrated in FIGS. 2 and 3, the inclined surfaces of ribs 46 can engage the outer surface of circumferentially extending wall 58 to limit lateral movement of the insert trays, but also the lateral surface 50 of a rib 46 the peak 48 of which is received in the groove 60 can act against the side of the circumferentially extending wall 38 facing into the groove 60. Accordingly, different sets of instruments can be stored in different insert trays 14 or 20, and the necessary insert trays be selected for the proper instruments stored therein and then installed in one base tray for sterilization. As discussed above, more than one of the smaller insert trays 20 may be installed in a single base tray; it is only necessary that one or more ribs on each of side walls 22, 24 be received in the groove 60 of the turned over portion.

We claim:

1. Sterilization container for sterilizing and storing medical instruments comprising a perforated base tray and a perforated insert tray, said base tray defining a cavity receiving said insert tray removably mounted in the cavity, the depth of the cavity of said base tray being greater than the depth of said insert tray whereby the insert tray fits within the cavity of the base tray to permit storage of instruments beneath said insert tray, said base tray and said insert tray including cooperating means carried on said base tray and said insert tray for supporting said insert tray within the base tray to prevent the insert tray from migrating to the bottom of the base tray, said insert tray having a dimension less than a corresponding dimension of said base tray whereby the insert tray is able to slide within said cavity, said cooperating means including stop means for limiting sliding of the insert tray within the base tray.

2. Sterilization container as claimed in claim 1, wherein said base tray has cooperating pairs of side walls defining said cavity, said cooperating means including means extending from a corresponding pair of side walls on the base tray.

3. Sterilization container as claimed in claim 2, wherein said cooperating means includes longitudinally spaced ribs projecting into said cavity from each of one pair of the cooperating pairs of base tray side walls, each of said ribs cooperating with the wall from which the rib projects to define a gap therebetween, said cooperating means including retention means on said insert tray received in said gap when the insert tray is installed in the base tray.

4. Sterilization container as claimed in claim 3, wherein said insert tray includes cooperating pairs of insert tray side walls defining an insert tray cavity, one pair of said cooperating pairs of insert tray side walls carrying said retention means.

5. Sterilization container as claimed in claim 4, wherein said retention means includes a turned over portion on each of the insert tray side walls, said turned over portion being turned out of said insert tray cavity, said turned over portion terminating in a circumferentially extending wall extending substantially parallel to the pairs of insert tray side walls, the turned over portion on one pair of insert tray side walls being received in said gap.

6. Sterilization container as claimed in claim 3, wherein said stop means includes a transversely projecting surface on said ribs projecting into said base tray cavity, and a cooperating surface on said insert tray extending transversely with respect to the base tray cavity for engagement with the transversely projecting surface on a corresponding rib.

7. Sterilization container for sterilizing and storing medical instruments comprising a base tray and a perforated insert tray, said perforated base tray having a base tray bottom and cooperating joining pairs of base tray side walls extending upwardly form said base tray bottom, said base tray side walls cooperating with said base tray bottom to define a base tray cavity receiving said insert tray, said insert tray having an insert tray bottom and cooperating joining pairs of insert tray side walls cooperating with the insert tray bottom to define an insert tray cavity which is smaller than said base tray cavity, one pair of said cooperating pairs of base tray walls having spaced ribs projecting into said cavity from each of said one pair of base tray walls, each of said ribs having a protruding peak cooperating with the wall from which the rib projects to define a gap therebetween, one of said corresponding pairs of said insert tray side walls having a portion defining a groove receiving said peaks to thereby support said insert tray.

8. Sterilization container as claimed in claim 7, wherein each of said ribs include a lateral engagement surface cooperating with a corresponding insert tray lateral engagement surface to prevent lateral shifting of the insert tray relative to the base tray in a given direction when the lateral engagement surface on the rib is in engagement with the lateral engagement surface on the insert tray.

9. Sterilization container as claimed in claim 8, wherein the insert tray walls have lower edges joined with the insert tray bottom and upper edges, the upper edges of said one pair of insert tray walls having a turned over portion turned out of said insert tray cavity and defining said groove.

10. Sterilization container as claimed in claim 8, wherein the insert tray walls have lower edges joined with the insert tray bottom and upper edges, the upper edges of said insert tray walls having a turned over portion turned out of said insert tray cavity, said turned over portion terminating in a circumferentially extending wall extending substantially parallel to the pairs of insert tray side walls and cooperating with the latter to define said groove.

11. Sterilization container as claimed in claim 10, wherein said circumferentially extending edge defines the insert tray lateral engagement surface.

12. Sterilization container as claimed in claim 10, wherein said protruding peaks are lower than the upper edge of the base tray, said turned over portion extending over said peaks and into said groove.

13. Sterilization container as claimed in claim 12, wherein said circumferentially extending edge is receive in said gap.

* * * * *